United States Patent
Zhang et al.

(10) Patent No.: US 10,455,776 B2
(45) Date of Patent: Oct. 29, 2019

(54) DYNAMIC DETECTION DEVICE FOR GROWTH OF POTTED CROP AND DETECTION METHOD THEREFOR

(71) Applicant: JIANGSU UNIVERSITY, Jiangsu (CN)

(72) Inventors: Xiaodong Zhang, Jiangsu (CN); Hanping Mao, Jiangsu (CN); Hongyan Gao, Jiangsu (CN); Zhiyu Zuo, Jiangsu (CN); Li Li, Jiangsu (CN); Yixue Zhang, Jiangsu (CN)

(73) Assignee: JIANGSU UNIVERSITY (CN)

( * ) Notice: Subject to any disclaimer, the term of this patent is extended or adjusted under 35 U.S.C. 154(b) by 255 days.

(21) Appl. No.: 15/525,894

(22) PCT Filed: Sep. 9, 2015

(86) PCT No.: PCT/CN2015/089213
§ 371 (c)(1),
(2) Date: May 10, 2017

(87) PCT Pub. No.: WO2016/074527
PCT Pub. Date: May 19, 2016

(65) Prior Publication Data
US 2017/0318757 A1 Nov. 9, 2017

(30) Foreign Application Priority Data
Nov. 10, 2014 (CN) .......................... 2014 1 0626853

(51) Int. Cl.
*A01G 9/26* (2006.01)
*G01B 11/08* (2006.01)
(Continued)

(52) U.S. Cl.
CPC ............... *A01G 9/26* (2013.01); *A01G 22/00* (2018.02); *A01G 25/16* (2013.01); *G01B 11/08* (2013.01);
(Continued)

(58) Field of Classification Search
None
See application file for complete search history.

(56) References Cited

U.S. PATENT DOCUMENTS

| | | | |
|---|---|---|---|
| 5,088,231 A * | 2/1992 | Kertz ..................... | A01C 1/042 47/1.01 R |
| 5,546,217 A * | 8/1996 | Greenway ............... | G01S 7/481 359/196.1 |

(Continued)

FOREIGN PATENT DOCUMENTS

| | | | | |
|---|---|---|---|---|
| CN | 101718522 | 6/2010 | ............. | G01B 11/00 |
| CN | 102384767 | 3/2012 | ............. | G01D 21/02 |

(Continued)

OTHER PUBLICATIONS

Jared Dale Hobeck, Energy Harvesting With Piezoelectric Grass for Autonomous Self-Sustaining Sensor Networks, 2014, 271 pages.*

(Continued)

*Primary Examiner* — Tung S Lau
(74) *Attorney, Agent, or Firm* — Hayes Soloway PC

(57) ABSTRACT

A dynamic detection device for the growth of a potted crop, includes a detection platform and a rotating shaft. A first cantilever frame is fixed at an upper portion of the rotating shaft; a laser ranging sensor is mounted at a tail end of the first cantilever frame; a second cantilever frame is fixed at a lower portion of the rotating shaft, and a pressure sensor is mounted at a tail end of the second cantilever frame. The detection platform has several bases; weight information crop is collected via a load sensor; stem diameter and plant
(Continued)

height information crop is collected via the pressure sensor, a photoelectric encoder and the laser ranging sensor; and growth information crop is described through information fusion, which can improve the efficiency and continuously monitor dynamic change information about the growth of a target crop in a growth process.

4 Claims, 1 Drawing Sheet

(51) Int. Cl.
*A01G 22/00* (2018.01)
*A01G 25/16* (2006.01)
*G01N 21/84* (2006.01)

(52) U.S. Cl.
CPC ..... *G01N 21/84* (2013.01); *G01N 2021/8466* (2013.01); *Y02A 40/274* (2018.01)

(56) References Cited

U.S. PATENT DOCUMENTS

| | | | | |
|---|---|---|---|---|
| 8,563,298 | B2* | 10/2013 | Lowery, Jr. | C12Q 1/6895 422/68.1 |
| 9,488,648 | B2* | 11/2016 | Neely | B82Y 25/00 |
| 2011/0247263 | A1* | 10/2011 | Hu | A01G 13/08 47/2 |
| 2017/0254789 | A1* | 9/2017 | Zuo | G01N 27/4035 |
| 2018/0007845 | A1* | 1/2018 | Martin | A01G 31/047 |
| 2018/0295792 | A1* | 10/2018 | Atwood | A01G 7/045 |

FOREIGN PATENT DOCUMENTS

| | | | | |
|---|---|---|---|---|
| CN | 102384787 | * | 3/2012 | |
| CN | 102636426 | | 8/2012 | G01N 19/00 |
| CN | 102967354 | | 3/2013 | G01B 11/02 |
| CN | 104457936 | | 3/2015 | G01B 11/02 |
| DE | 102010048298 | | 4/2012 | G06K 9/62 |
| JP | H08266153 | | 10/1996 | A01G 7/00 |

OTHER PUBLICATIONS

Sensor technologies 2013, 321 pages.*
International Preliminary Report on Patentability issued in application No. PCT/CN2015/089213, dated May 16, 2017 (13 pgs).
International Search Report and Written Opinion issued in application No. PCT/CN2015/089213, dated Dec. 3, 2015 (20 pgs).

* cited by examiner

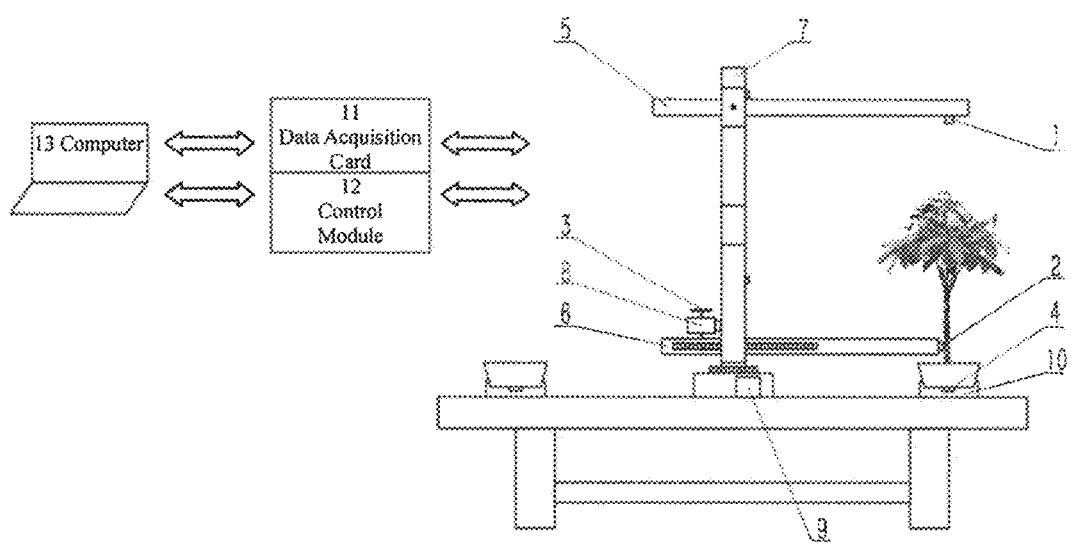

DYNAMIC DETECTION DEVICE FOR GROWTH OF POTTED CROP AND DETECTION METHOD THEREFOR

I. TECHNICAL FIELD

The present invention relates to a dynamic detection device for the growth of a crop and a detection method thereof, which are applicable to the technical field of potted crops.

II. BACKGROUND ART

Crop growth information monitoring is an important basis for scientific decision-making for irrigation and fertilization. Stem diameter, plant height, and biomass are important indexes that reflect the growth of a crop. By detecting those indexes scientifically, a scientific basis can be provided for irrigation and fertilization management, and yield pre-estimation in the crop growth process.

At present, crop growth detection is mainly carried out manually. For example, in a biomass detection process, the biomass of a crop in different growth stages must be measured by weighing after harvesting. Such a sampling and measuring approach is time-consuming and labor-intensive. Since the samples measured for biomass in different growth stages are not from the same sample, the accuracy of crop biomass measurement is affected by the differences in crop growth between different samples. The Patent Application No. CN201210078528.1 has disclosed a handheld biomass testing device and a testing method, in which the resilience force produced during crop deformation is acquired by means of a pressure sensor, and thereby the biomass of a field crop is detected. The device is applicable to biomass detection for a small population of crops in a small plot in a breeding process. However, it is difficult to monitor the individual growth information of a potted crop dynamically and continuously with the device and method owing to the difference in detection mode. The Patent Application No. CN201210430049.1 has disclosed a crop growth information detection device and a detection method, wherein, the device is applicable to detection of plant height and stem diameter of a crop that has multiple stems per single plant during natural growth, such as wheat and paddy rice, etc., but can't be used to monitor the growth of a potted crop dynamically and continuously. In summary, it is difficult to detect the biomass information and dynamic change process of a potted crop continuously and dynamically with existing crop growth detection devices and methods in the prior art due to the limitation of the existing crop growth devices and methods. The existing crop growth detection devices and methods can't meet the demand for quasi-real-time accurate and dynamic monitoring of the growth of a potted crop in the modern large-scale production process.

III. CONTENTS OF THE INVENTION

The object of the present invention is to provide a dynamic detection device and a detection method for the growth of a crop, so as to realize lossless dynamic detection of potted crop.

To attain the object described above, the present invention employs the following technical scheme: a dynamic detection device for the growth of a potted crop, comprising a detection platform and a rotating shaft, wherein, a rotating motor is mounted on a bottom end of the rotating shaft and configured to drive the rotating shaft to rotate; a first cantilever frame is fixed to a top part of the rotating shaft, and a laser ranging sensor is mounted at a tail end of the first cantilever frame; a second cantilever frame is fixed to a bottom part of the rotating shaft, and a first step motor is fixed to the rotating shaft and configured to drive the second cantilever frame to move left and right via a gear-and-rack device; a pressure sensor is mounted at a tail end of the second cantilever frame; a second step motor is arranged on the detection platform and configured to drive the rotating shaft to move left and right via the gear-and-rack device; the detection platform is further provided with several bases, each of which is provided with a load sensor, and the bases are arranged circularly along the rotating shaft.

In the scheme described above, the first step motor is further provided with a photoelectric encoder, which is configured to measure the displacement of the second cantilever frame by detecting the number of turns of rotation of the first step motor and thereby accomplish the measurement of stem diameter of a potted crop sample.

In the scheme described above, the device further comprises a signal transmission and processing system, which comprises a data acquisition card, a control module, and a computer, wherein, the data acquisition card is configured to transmit the signals of the laser ranging sensor, the pressure sensor, the photoelectric encoder, and the load sensor to the control module, the control module is connected with the computer and configured to control the rotating motor, the first step motor 8, and the second step motor.

In the scheme described above, the first cantilever frame and the second cantilever frame are detachably fixed to the rotating shaft, and can be mounted on the rotating shaft at different positions, depending on the type of the potted crop sample. However, for the dynamic detection device for the growth of a potted crop, in each dynamic detection period, the types of the potted crops to be detected on the detection platform are the same.

The present invention further provides a method that utilizes the dynamic detection device for the growth of a potted crop to detect the growth of a potted crop dynamically, which comprises the following steps:

A. presetting of a multi-sensor detection device
  (1) employing a blank sample as a calibration sample, adjusting the blank sample and potted crop samples so that they have the same amount of matrix material, water and fertilizer, and employing the same fertilization and irrigation measures for the samples;
  (2) placing the blank sample and the potted crop samples on the bases;
  (3) adjusting the position of the first cantilever frame according to the demand of the potted crop samples so that the laser ranging sensor is located right above the potted crop samples, and adjusting the position of the second cantilever frame so that the pressure sensor is located at the stems of the potted crop samples; setting an initial position of the second cantilever frame that is provided with the pressure sensor, so that the outermost edge of the pressure sensor is tangent to a circle formed by all potted crop samples;
  (4) calibrating the load sensor arranged between the base and the blank sample;
  (5) setting the initial positions of the electric motors on the computer according to the demand for detection, and determining the rotation angles, start times and cycle times;

B. starting the dynamic detection device for the growth of a potted crop to detect the growth of the crop first, acquiring the mass information of the blank sample with the dynamic detection device for the growth of a potted crop; then, moving the sensors of the dynamic detection device for the growth of a potted crop to preset positions in an order preset on the computer to execute detection after the reference information is determined, accomplishing acquisition of crop mass, stem diameter, and plant height information in one cycle period, and then resetting; next, repeating the above-mentioned detection process according to the preset cycle time; thus, the dynamic detection of crop growth information is accomplished;

C. quantizing and describing characteristic parameters of growth of the potted crop samples (1) calculating the difference between the mass information acquired with the load sensor for each potted crop sample and the mass information acquired with the load sensor for the blank sample, to obtain the change of crop biomass;

(2) extracting characteristic parameters (stem diameter and plant height) from the information of the potted crop samples acquired with the laser ranging sensor 1 and the pressure sensor 2;

(3) quantizing, describing, and outputting growth change information in the crop growth process by means of information fusion, according to the change of acquired information of stem diameter, plant height, and biomass.

Beneficial effects: (1) The present invention can detect the growth information of the same type of crops dynamically in real time, without damaging the crops. By detecting the stem diameter, plant height and biomass of the crop with multiple mechanical-optical sensors, not only the crop growth can be detected quickly, effectively, and losslessly in real time, but also the crop growth information can be monitored continuously and dynamically. This is also a future developing trend of digital agriculture. (2) The present invention incorporates load sensor, pressure sensor, photoelectric encoder, and laser ranging sensor to monitor the stem diameter, plant height and biomass of a crop continuously and dynamically. The weight information of the crop is acquired with the load sensor, the stem diameter and plant height information of the crop is acquired with the pressure sensor, photoelectric encoder, and laser ranging sensor, and the growth information of the crop is described by mechanical-optical multi-information fusion. (3) Compared with the conventional manual detection method, the present invention not only can improve efficiency, but also can monitor the dynamically changed information of a target crop in the growth process. Compared with remote sensing monitoring methods, such as optical spectrum-based or image-based monitoring methods, the present invention is less susceptible to environmental factors, such as light irradiation and complex background, etc.

IV. DESCRIPTION OF DRAWINGS

FIG. 1 is a structural diagram of a dynamic detection device for the growth of a crop, which is based on the information acquired with multiple mechanical-optical sensors.

In the FIGURE: 1—laser ranging sensor; 2—pressure sensor; 3—photoelectric encoder; 4—load sensor; 5—first cantilever frame; 6—second cantilever frame; 7—rotating shaft; 8—first step motor; 9—second step motor; 10—base; 11—data acquisition card; 12—control module; 13—computer.

V. EMBODIMENTS

The technical scheme of the dynamic detection device for the growth of a crop, which is based on the information acquired with multiple mechanical-optical sensors, is as follows:

1) Presetting of a multi-sensor detection device (1) The device can carry out sampling and monitoring for three crop samples at the same time, and employs a blank sample as a calibration sample. Adjustment is made so that the blank sample and crop samples have the same amount of matrix material and water and fertilizer, and the same fertilization and irrigation measures are used for the samples.

(2) The samples are placed on a load sensing device, and are locked by means of locking devices, wherein, the blank sample is placed at the last position.

(3) The position of the rotating arm of the laser ranging sensor is adjusted so that the laser ranging sensor is located right above the crop, and then the relative position of the laser ranging sensor is fixed by means of fastening bolts; the vertical position of the rotating arm of the pressure sensor is adjusted so that the pressure sensor is located at the stem of the crop.

(4) Calibrating the load sensor for the blank sample (5) The initial detection position and rotation angle of the multi-sensor detection device provided with mechanical rotating arm are set; the initial position of the rotating arm mounted with pressure sensor is set so that the outmost edge of the pressure sensor is tangent to a circle formed by the four samples; the cycle time and start time are set according to the demand for detection.

2) Starting multi-sensor detection device to detect the growth of the crops

First, the mass information of the blank sample is acquired with the detection device; then, the detection device is moved to preset positions in a preset order to execute detection after the reference information is determined, the acquisition of crop mass, stem diameter, and plant height information is accomplished in one cycle period, and then the detection device is reset; next, the above-mentioned detection process is repeated according to the preset cycle time; thus, the dynamic detection of crop growth information is accomplished.

3) Quantizing and describing characteristic parameters of growth of the crop (1) The difference between the mass information acquired with the load sensor for each crop sample and the mass information acquired with the load sensor for the blank sample is calculated, to obtain the change of crop biomass.

(2) Extracting characteristic parameters (stem diameter and plant height) from the crop sample information acquired with the sensors (3) The growth change information in the crop growth process is quantized, described and output by means of multi-information fusion, according to the change of acquired information of stem diameter, plant height, and biomass.

The dynamic detection device for the growth of a crop provided in the present invention, which is based on information acquired with multiple mechanical-optical sensors, utilizes a synergetic effect among multiple sensors and mechanical devices to detect crop growth information dynamically.

The dynamic detection device for the growth of a crop, which is based on information acquired with multiple mechanical-optical sensors, comprises a detection platform, a multi-sensor information acquisition device, and a control system.

The detection platform comprises a rotating shaft, cantilever frames, and a base.

The rotating shaft is driven by a step motor fixed to the base of the detection platform, a driven gear is mounted on the rotating shaft, and the detection platform is driven by a pair of gears to rotate.

The cantilever frames include a cantilever frame for plant height detection and a cantilever frame for stem diameter detection, wherein, a laser ranging sensor is mounted on the cantilever frame for plant height detection, the height of the cantilever frame for plant height detection can be adjusted in vertical direction, and the extension of the cantilever arm of the cantilever frame for plant height detection can be adjusted in horizontal direction. A pressure sensor is mounted on the cantilever frame for stem diameter detection, the height of the cantilever frame for stem diameter detection can be adjusted in vertical direction, the extension of the cantilever arm of the cantilever frame for stem diameter detection is controlled by another step motor fixed to the rotating shaft, a part of the cantilever arm is manufactured into a toothed rack, so that the cantilever arm can move horizontally by virtue of gear-and-rack transmission. A photoelectric encoder is mounted on one end of the step motor, and is configured to measure the displacement of the cantilever arm by detecting the rotation circles of the step motor and thereby measure the stem diameter of the crop.

The load sensor 4 is arranged right below the crop and mounted between the crop and the base 10. Total four sets of bases are provided and are distributed on a square detection platform in diameter of 3 m. The bases are configured to acquire mass information of the crop. In view that the mass acquired by means of the base includes mass of pot, mass of matrix material, and mass of nutrient solution, etc., and the volatilization of the matrix material and nutrient solution during the entire growth process of the crop has influence on the detection accuracy of crop biomass, a calibration pot that only contains matrix material and nutrient solution without crop is provided in the actual detection process, and the initial mass of the calibration plot is the same as the mass of a blank sample culture device.

The multi-sensor information acquisition device comprises a load sensor, a pressure sensor, a photoelectric encoder, a laser ranging sensor, and a data acquisition card. The load sensor, pressure sensor, photoelectric encoder, and laser ranging sensor are connected with the data acquisition card through coax signal cables, and the data acquisition card is connected with the computer through a USB bus.

The control system comprises a control module and a computer. The control module is connected with the computer through a USB bus and connected with the two step motors via I/O interface, so that the movement of the step motors is controlled by commands issued from the computer. Whenever the cantilever frame for stem diameter detection is to detect the next crop, the step motor is controlled to drive the cantilever frame to retract away from the position at the stem of the crop, and the other step motor is controlled to drive the rotating shaft to the next detection position.

Hereunder the present invention will be described in details with reference to the accompanying drawing and implementation steps.

As shown in FIG. 1, the dynamic detection device for the growth of a crop provided in the present invention, which is based on information acquired with multiple mechanical-optical sensors, comprises a detection platform, a multi-sensor information acquisition device, and a control system.

Wherein, the detection platform is provided with a rotating shaft 7, a first cantilever frame 5, a second cantilever frame 6, and a base 10.

Wherein, the rotating shaft 7 may be driven to rotate by a rotating motor mounted on the bottom, the second step motor 9 is fixed to the base of the detection platform, a driving gear is mounted on a rotating output shaft of the second step motor 9, a driven toothed rack is mounted on the rotating shaft 7, and the second step motor 9 drives the rotating shaft 7 to move left and right by means of gear-and-rack transmission. Wherein, a first cantilever frame 5 for plant height detection and a second cantilever frame 6 for stem diameter detection are arranged on the rotating shaft 7. A laser ranging sensor 1 is mounted on the first cantilever frame 5. The first cantilever frame 5 is detachably fixed to the rotating shaft 7, e.g., socket-jointed to the rotating shaft 7; preferably, the rotating shaft 7 is arranged with a mounting groove, and the first cantilever frame 5 is socket-jointed to the rotating shaft 7. The first cantilever frame 5 may be socket-jointed to the rotating shaft 7 at different height in the vertical direction according to the actual requirement of the potted crop to be measured, and the first cantilever frame 5 and the rotating shaft 7 move left and right together under the action of the second step motor 9. A pressure sensor 2 is mounted on the second cantilever frame 6. The second cantilever frame 6 is mounted to the rotating shaft 7 essentially in the same way as the first cantilever frame 5, and the left/right extension of the second cantilever frame 6 is controlled by the first step motor 8. The first step motor 8 is fixed to the rotating shaft 7, a part of the second cantilever frame 6 is manufactured into a toothed rack, a gear is mounted on an output shaft of the first step motor 8, and the cantilever arm of the second cantilever frame 6 moves horizontally by means of gear-and-rack transmission. A photoelectric encoder 3 is mounted on one end of the first step motor 8, and is configured to measure the displacement of the cantilever arm of the second cantilever frame 6 by detecting the number of turns of rotation of the first step motor 8 and thereby measure the stem diameter of the crop, wherein, the load sensor 4 is arranged right below the crop and mounted between the crop and the base 10.

Wherein, four sets of bases 10 are provided and are distributed on a square detection platform in diameter of 3 m. The bases 10 are configured to acquire mass information of the crop. In view that the mass acquired by means of the base includes mass of pot, mass of matrix material, and mass of nutrient solution, etc., and the volatilization of the matrix material and nutrient solution during the entire growth process of the crop has influence on the detection accuracy of crop biomass, a calibration pot that only contains matrix material and nutrient solution without crop is provided in the actual detection process, and the initial mass of the calibration plot is the same as the mass of a blank sample culture device.

Wherein, the multi-sensor information acquisition device comprises a load sensor 4, a pressure sensor 2, a photoelectric encoder 3, a laser ranging sensor 1, and a data acquisition card 11. The load sensor 4, pressure sensor 2, photoelectric encoder 3, and laser ranging sensor 1 are connected with the data acquisition card 11 through coax signal cables, and the data acquisition card 11 is connected with the computer 13 through a USB bus.

Wherein, the control system comprises a control module 12 and a computer 13. The control module 12 is connected with the computer 13 through a USB bus and connected with two step motors 8 and 9 via I/O interface, so that the movement of the step motors 8 and 9 is controlled by commands issued from the computer 13. Whenever the second cantilever frame for stem diameter detection 6 is to detect the next crop, the first step motor 8 is controlled to drive the second cantilever frame 6 to retract away from the position at the stem of the crop, and the other step motor is controlled to drive the rotating shaft to the next detection position.

As shown in FIG. 1, the technical scheme of the multi-sensor biomass detection device with a mechanical rotating arm provided in the present invention is as follows:

1) Presetting of a multi-sensor detection device
   (1) The device can carry out sampling and monitoring for three potted crop samples at the same time, and employs a blank sample as a calibration sample. Adjustment is made so that the blank sample and crop samples have the same amount of matrix material and water and fertilizer, and the same fertilization and irrigation measures are used.
   (2) The samples are placed on a load sensing device 10, and are locked by means of locking devices, wherein, the blank sample is placed at the last position.
   (3) The position of the rotating arm of the laser ranging sensor 1 is adjusted so that the laser ranging sensor is located right above the crop, and then the relative position of the laser ranging sensor is fixed by means of fastening bolts; the vertical position of the rotating arm of the pressure sensor 2 is adjusted so that the pressure sensor 2 is located at the stem of the crop.
   (4) Calibrating the load sensor 4 for the blank sample
   (5) The initial detection position and rotation angle of the multi-sensor detection device with mechanical rotating arm are set; the initial position of the rotating arm 6 mounted with pressure sensor is set so that the outmost edge of the pressure sensor 2 is tangent to a circle formed by the three potted crop samples and the one blank sample; the cycle time and start time are set according to the demand for detection.

2) Starting multi-sensor detection device to detect the growth of the crops

First, the mass information of the blank sample is acquired with the detection device; then, the detection device is moved to preset positions in a preset order to execute detection after the reference information is determined, the acquisition of crop mass, stem diameter, and plant height information is accomplished in one cycle period, and then the detection device is reset; next, the above-mentioned detection process is repeated according to the preset cycle time; thus, the dynamic detection of crop growth information is accomplished.

3) Quantizing and describing characteristic parameters of growth of the crop
   (1) The difference between the mass information acquired with the load sensor for each crop sample and the mass information acquired with the load sensor for the blank sample is calculated, to obtain the change of crop biomass.
   (2) Extracting characteristic parameters (stem diameter and plant height) from the crop sample information acquired with the sensors
   (3) The growth change information in the crop growth process is quantized, described and output by means of multi-information fusion, according to the change of acquired information of stem diameter, plant height, and biomass.

The invention claimed is:

1. A dynamic detection device for the growth of a potted crop, comprising a detection platform and a rotating shaft, wherein, a rotating motor is mounted on a bottom end of the rotating shaft and configured to drive the rotating shaft to rotate;
   a first cantilever frame is fixed to a top part of the rotating shaft, and a laser ranging sensor is mounted at a tail end of the first cantilever frame;
   a second cantilever frame is fixed to a bottom part of the rotating shaft, and a first step motor is fixed to the rotating shaft and configured to drive the second cantilever frame to move left and right via a gear-and-rack device;
   a pressure sensor is mounted at a tail end of the second cantilever frame;
   a second step motor is arranged on the detection platform and configured to drive the rotating shaft to move left and right via the gear-and-rack device;
   wherein the detection platform is further provided with several bases, each of which is provided with a load sensor, and the bases are arranged circularly along the rotating shaft.

2. The dynamic detection device for the growth of a potted crop according to claim 1, wherein,
   the first step motor is further provided with a photoelectric encoder, which is configured to measure the displacement of the second cantilever frame by detecting a number of turns of rotation of the first step motor and thereby accomplish the measurement of stem diameter of a potted crop sample.

3. The dynamic detection device for the growth of a potted crop according to claim 2, further comprising a signal transmission and processing system, which comprises a data acquisition card, a control module, and a computer, wherein,
   the data acquisition card is configured to transmit the signals of the laser ranging sensor, the pressure sensor, the photoelectric encoder, and the load sensor to the control module, the control module is connected with the computer and configured to control the rotating motor, the first step motor, and the second step motor.

4. The dynamic detection device for the growth of a potted crop according to claim 3, wherein,
   the first cantilever frame and the second cantilever frame are detachably fixed to the rotating shaft, and can be mounted on the rotating shaft at different positions, depending on the type of the potted crop sample.

* * * * *